United States Patent
Landgrebe et al.

(10) Patent No.: US 11,006,954 B2
(45) Date of Patent: May 18, 2021

(54) SUCTION ATTACHMENT OF AN ADJUNCT TO A SURGICAL INSTRUMENT

(71) Applicant: Ethicon LLC, Guaynabo, PR (US)

(72) Inventors: Susanne Landgrebe, Sulfeld (DE); Michael J. Vendely, Lebanon, OH (US); Charles J. Scheib, Loveland, OH (US); Frederick E. Shelton, IV, Hillsboro, OH (US); Jason L. Harris, Lebanon, OH (US); Joerg Priewe, Norderstedt (DE)

(73) Assignee: Ethicon LLC, Guaynabo, PR (US)

( * ) Notice: Subject to any disclaimer, the term of this patent is extended or adjusted under 35 U.S.C. 154(b) by 654 days.

(21) Appl. No.: 15/436,119

(22) Filed: Feb. 17, 2017

(65) Prior Publication Data
US 2018/0235615 A1 Aug. 23, 2018

(51) Int. Cl.
*A61B 17/072* (2006.01)
*A61B 17/00* (2006.01)

(52) U.S. Cl.
CPC ...... *A61B 17/072* (2013.01); *A61B 17/07207* (2013.01); *A61B 17/07292* (2013.01); *A61B 2017/0046* (2013.01); *A61B 2017/00477* (2013.01); *A61B 2017/00893* (2013.01);
(Continued)

(58) Field of Classification Search
CPC ........ A61B 2017/00544; A61B 17/072; A61B 17/07292; A61B 2017/0046; A61B 2017/00477; A61B 2017/00893; A61B 2017/07257; A61B 2017/07271; A61B 17/07207
See application file for complete search history.

(56) References Cited

U.S. PATENT DOCUMENTS

| | | | |
|---|---|---|---|
| 7,143,925 B2 | 12/2006 | Shelton, IV et al. | |
| 7,601,118 B2 | 10/2009 | Smith et al. | |
| 8,317,070 B2 | 11/2012 | Hueil et al. | |
| (Continued) | | | |

FOREIGN PATENT DOCUMENTS

| | | | |
|---|---|---|---|
| EP | 2644125 A2 | 10/2013 | |
| EP | 2644126 A2 | 10/2013 | |

OTHER PUBLICATIONS

Extended European Search Report for EP App. No. 18157205.8 dated Jul. 9, 2018 (6 pages).

*Primary Examiner* — Todd J Scherbel
*Assistant Examiner* — Mikail A Mannan
(74) *Attorney, Agent, or Firm* — Mintz Levin Cohn Ferris Glovsky and Popeo, P.C.

(57) ABSTRACT

Adjuncts for use with surgical instruments, such as staplers, are provided. In one embodiment, an adjunct can include a plurality of suction members configured to attach the adjunct to an end effector jaw of a surgical stapler using a suction force. The suction members can be configured to generate the suction force when compressed. The suction members can be further configured to release the suction force to decouple the adjunct from the end effector jaw, permitting deployment of the adjunct at a treatment site. In certain embodiments, the suction members can include a plurality of air pockets formed in the bulk of the adjunct or within protrusions extending outward from a surface of the adjunct. The air pockets can be in communication with corresponding openings allowing air to escape the air pockets when compressed.

15 Claims, 8 Drawing Sheets

(52) U.S. Cl.
CPC ............... *A61B 2017/07257* (2013.01); *A61B 2017/07271* (2013.01)

(56) References Cited

U.S. PATENT DOCUMENTS

| | | |
|---|---|---|
| 8,393,514 B2 | 3/2013 | Shelton, IV et al. |
| 9,282,962 B2 | 3/2016 | Schmid et al. |
| 2013/0221065 A1 | 8/2013 | Aronhalt et al. |
| 2013/0256367 A1* | 10/2013 | Scheib ................. A61B 17/068 227/175.1 |
| 2013/0256373 A1* | 10/2013 | Schmid ............ A61B 17/07207 227/176.1 |
| 2013/0256377 A1 | 10/2013 | Schmid et al. |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0134077 A1 | 5/2015 | Shelton, IV et al. |
| 2015/0136831 A1* | 5/2015 | Baxter, III ......... A61B 17/0644 227/176.1 |
| 2015/0272575 A1 | 10/2015 | Leimbach et al. |
| 2015/0277471 A1 | 10/2015 | Leimbach et al. |
| 2015/0351758 A1 | 12/2015 | Shelton, IV et al. |
| 2016/0089142 A1 | 3/2016 | Harris et al. |
| 2017/0055986 A1 | 3/2017 | Harris et al. |

\* cited by examiner

SUCTION ATTACHMENT OF AN ADJUNCT TO A SURGICAL INSTRUMENT

FIELD

Methods and devices are provided for attaching an adjunct to a surgical instrument using various suction techniques.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the holes formed when staples penetrate the tissue or other object in which it is disposed. Blood, air, gastrointestinal fluids, and other fluids can seep through the openings formed by the staples, even after the staple is fully formed. The tissue being treated can also become inflamed due to the trauma that results from stapling. Still further, staples, as well as other objects and materials that can be implanted in conjunction with procedures like stapling, generally lack some characteristics of the tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

Accordingly, there remains a need for improved devices and methods for stapling tissue, blood vessels, ducts, shunts, or other objects or body parts such that leaking and inflammation is minimized while substantially maintaining the natural characteristics of the treatment region.

SUMMARY

Methods and devices are provided for attaching an adjunct to a surgical stapling device=. In one embodiment, a surgical stapling device is provided and includes an elongate shaft having an end effector with first and second jaws configured to grasp tissue therebetween. The surgical stapling device further includes an adjunct positioned on the first jaw and held on the first jaw by a suction force.

The end effector and the adjunct can have a variety of configurations. In one embodiment, the end effector can be configured to fire a plurality of staples through the adjunct to release the suction force and thereby cause the adjunct to be released from the end effector.

In another aspect, the adjunct can include a plurality of voids formed therein that are configured to generate the suction force when compressed that cause the adjunct to engage the first jaw by suction. The adjunct can include first and second layers laminated together, where the plurality of voids can be formed in the first layer and the first layer can be positioned in contact with a surface of the first jaw. The end effector can be configured to fire a plurality of staples through the adjunct such that the plurality of staples penetrate the plurality of voids to break the suction force and release the adjunct from the end effector.

In a further aspect, the first jaw can include an anvil having a plurality of staple-receiving cavities formed therein and the adjunct can include a plurality of voids that are aligned with the plurality of staple-receiving cavities. Compression of the plurality of voids into the staple-receiving cavities can be configured to generate the suction force that causes the adjunct to engage the first jaw.

In an additional aspect, the first jaw can include an anvil having a plurality of staple-receiving cavities formed therein and the adjunct can include a plurality of protrusions formed thereon that can be configured to extend into the plurality of staple-receiving cavities, where each protrusion can have a void formed therein that is configured to generate the suction force when compressed to cause the adjunct to engage the first jaw. The first jaw can include a plurality of alignment features configured to align the plurality of protrusions with the plurality of staple-receiving cavities.

In another embodiment, an adjunct for use with a surgical stapling device is provided and includes a flexible laminated adjunct formed from at least one of a synthetic material and a biologic material. The adjunct includes a first layer coupled to a second layer, where the first layer has a plurality of openings. The first layer can be positioned on the second layer such that the plurality of openings form a plurality of air pockets between the first and second layers. The adjunct can be configured to engage a surface of a jaw on a surgical stapling device by compressing the adjunct against the surface to generate a partial vacuum within each air pocket.

The first and second layers of the adjunct can have a variety of configurations. In one embodiment, the first layer can be elastically deformable. The first layer can include a plurality of protrusions formed therein, each protrusion defining one of the plurality of air pockets, and each protrusion can have one of the plurality of openings formed therein. The plurality of openings can be configured to align with a plurality of staple-receiving cavities formed in an anvil of a surgical stapler. Compression of the adjunct can be configured to cause air in the plurality of air pockets to flow out of the plurality of openings to generate the partial vacuum. The second adjunct layer can include a solid, non-permeable, void-free layer.

In another embodiment, a surgical method is provided and includes positioning an adjunct on a first jaw of an end effector of a surgical device and compressing the adjunct against the first jaw to cause a plurality of suction members on the adjunct to generate suction that secures the adjunct to the first jaw.

The method can have a variety of configurations. In one embodiment, compressing the adjunct against the first jaw can cause air to be released from the plurality of suction members such that a partial vacuum is created within the plurality of suction members. The plurality of suction members can include a plurality of hollow protrusions, each protrusion having an opening formed thereon that is positioned against a surface of the first jaw. The plurality of suction members can be aligned with a plurality of staple-receiving cavities on the first jaw.

In other aspects, the method includes firing a plurality of staples from the end effector, the plurality of staples penetrating the plurality of suction members to cause the suction to be released, thereby causing the adjunct to be released from the end effector.

BRIEF DESCRIPTION OF DRAWINGS

This invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It can be desirable to use one or more biologic materials and/or synthetic materials, collectively referred to herein as "adjuncts," in conjunction with surgical instruments to help improve surgical procedures. While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct(s) can be configured to wick or absorb beneficial fluids, e.g., sealants, blood, glues, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts. The adjunct(s) may also affect tissue growth through the spacing, positioning and/or orientation of any fibers or strands associated with the adjunct(s). Furthermore, in some circumstances, an adjunct can be useful in distributing pressure applied by the staple thereby reducing the possibility of a staple pulling through a tissue (which can be friable) and failing to fasten the tissue as intended (so-called "cheese wiring"). Additionally, the adjunct can be at least partially stretchable and can thus allow at least partial natural motion of the tissue (e.g., expansion and contraction of lung tissue during breathing). In some embodiments, a staple line can be flexible as described, for example, in U.S. Pat. Pub. No. 2016/0089142 entitled "Method for Creating a Flexible Staple Line," filed on Sep. 26, 2014, which is hereby incorporated by reference herein in its entirety.

Surgical Stapling Instruments

A variety of surgical instruments can be used in conjunction with the adjunct(s) and/or medicant(s) disclosed herein. "Adjuncts" are also referred to herein as "adjunct materials." The surgical instruments can include surgical staplers. A variety of surgical staplers can be used, for example linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife blade or other cutting element capable of creating a cut inside of the rows of staples to define an opening through tissue held within the jaws. The staplers can be on a variety of tissues in a variety of different surgical procedures, for example in thoracic surgery or in gastric surgery.

Figure 1:
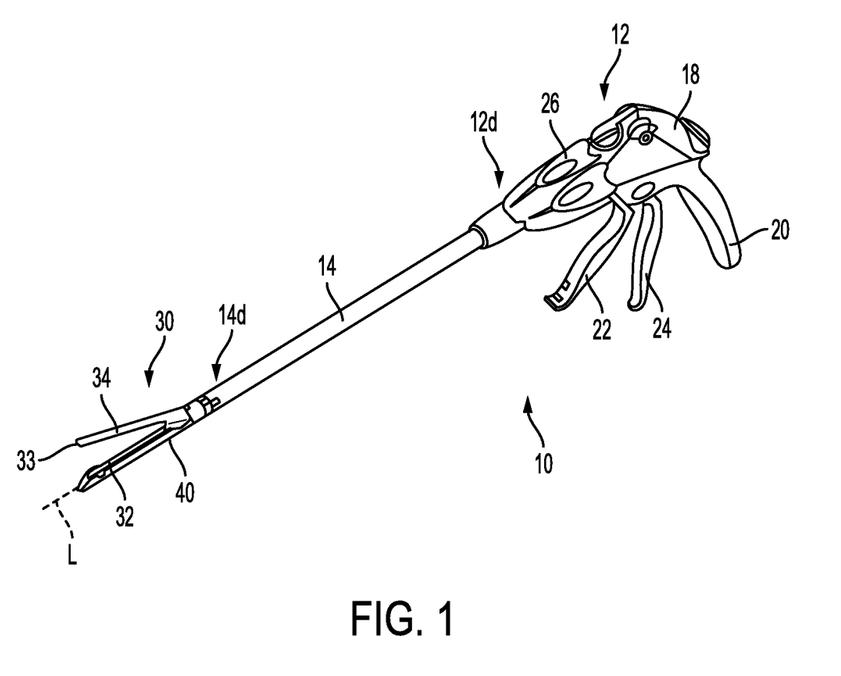
FIG. 1 is a perspective view of one embodiment of a surgical stapler.
Figure 2:
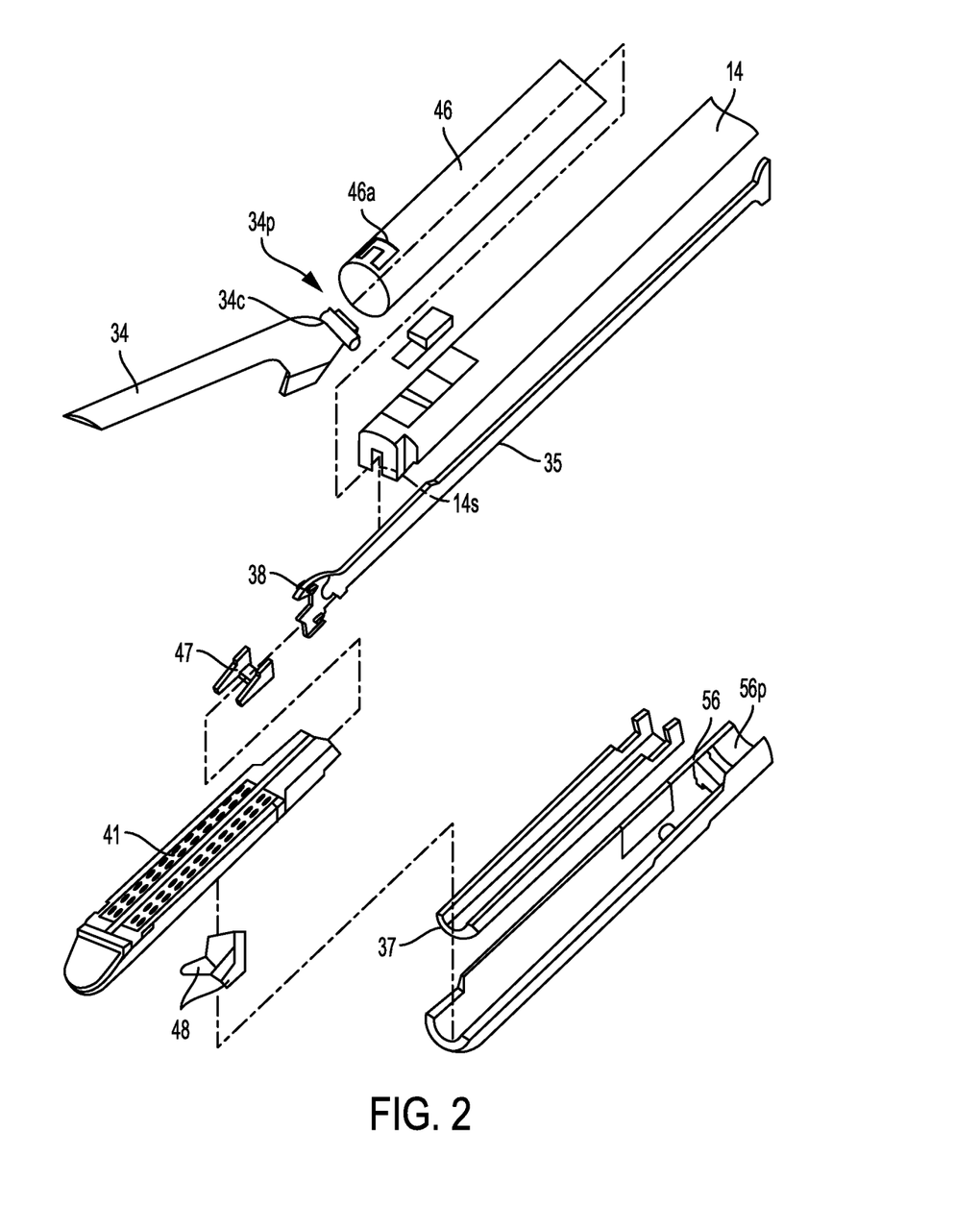
FIG. 2 is an exploded view of a distal portion of the surgical stapler of FIG. 1.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. As shown in FIG. 2, the lower jaw 32 has a staple channel 56 (see FIG. 2) configured to support a staple cartridge 40, and the upper jaw 34 has an anvil or tissue contacting surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 (see FIG. 3) or other cutting element can be associated with the firing system to cut tissue during the stapling procedure. The cutting element can be configured to cut tissue at least partially simultaneously with the staples being ejected. In some circumstances, it may be advantageous if the tissue is cut after the staples have been ejected and the tissue is secured. Thus, if a surgical procedure requires that a tissue captured between the jaws be severed, the knife blade 36 is advanced to sever the tissue grasped between the jaws after the staples have been ejected from the staple cartridge 40.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent the distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple-receiving cavities (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement to the shaft 14. When the upper jaw 34 is pivoted downwardly, the upper jaw 34 moves the anvil surface 33 and the staple-receiving cavities formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
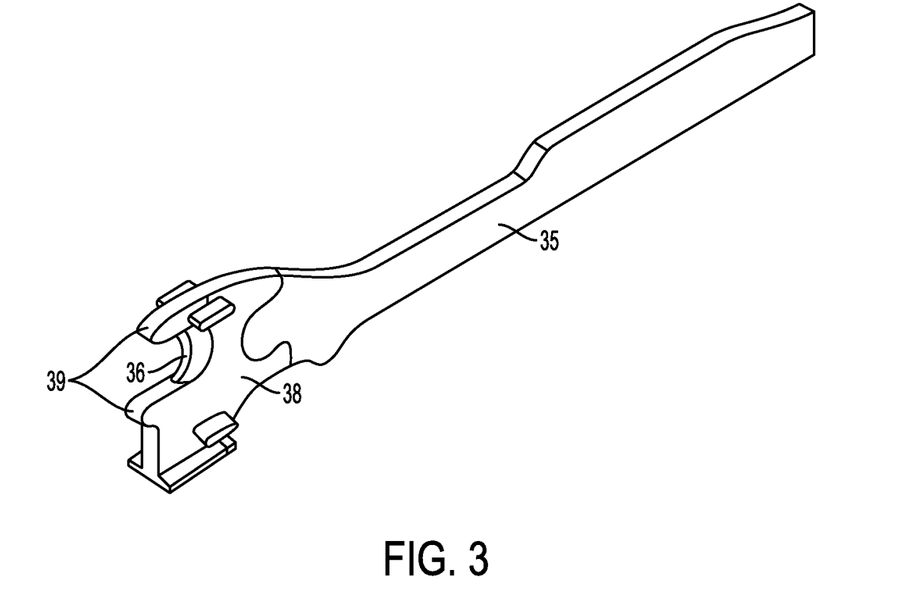
FIG. 3 is a perspective view of a firing bar of the surgical stapler of FIG. 1.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47, shown in FIG. 2, which in turn can push staple drivers 48 upwardly through pockets 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the lower and upper jaws 32, 34 to compress the jaws 32, 34 toward one another as the firing bar 35 advances through the end effector 30. Simultaneously, the knife blade 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32, 34 at the surgical site and the tissue with respect to the jaws 32, 34. After appropriate positioning has been achieved, the clamping trigger 22 can be pulled toward the stationary handle 20 to actuate the clamping system. The clamping trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the firing trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
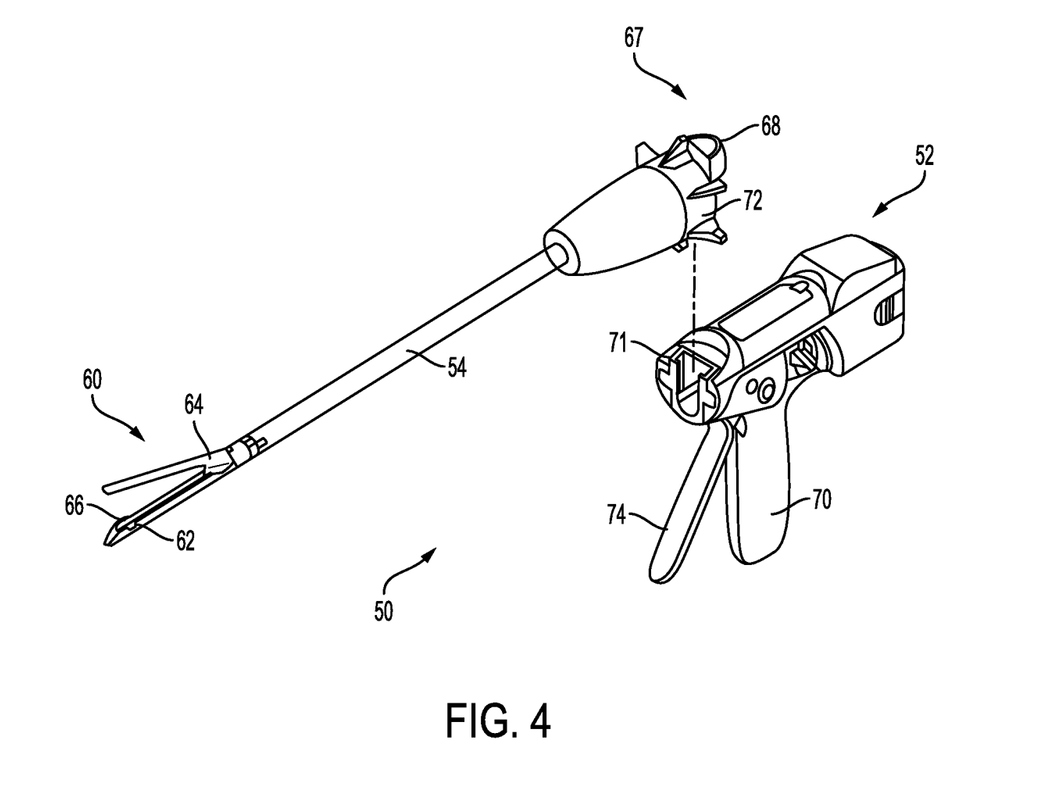
FIG. 4 is a perspective disassembled view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 64 can move to move the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

In further embodiments, the surgical instrument can adopt other forms. In one example, the surgical instrument is in the form of a circular surgical stapler (not shown). The circular stapler can generally be configured and used similarly to the linear staplers 10, 50 of FIGS. 1 and 4, but with some features accommodating its functionality as a circular stapler, such as a cartridge assembly configured to deploy staples against a circular anvil to form a circular pattern of staples, e.g., staple around a circumference of a tubular body organ.

The illustrated examples of surgical stapling instruments 10, 50 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2015/0277471 entitled "Systems And Methods For Controlling A Segmented Circuit" and filed Mar. 26, 2014, U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. Pat. Pub. No. 2015/0272575, entitled "Surgical Instrument Comprising a Sensor System," and filed on Mar. 26, 2014, and U.S. Pat. Pub. No. 2015/0351758, entitled "Adjunct Materials and Methods of Using Same in Surgical Methods for Tissue Sealing," and filed on Jun. 10, 2014, which are hereby incorporated by reference herein in their entireties.

Implantable Adjuncts

As indicated above, various implantable adjuncts are provided for use in conjunction with surgical stapling instruments. The adjuncts can have a variety of configurations, and can be formed from various materials. In general, an adjunct can be formed from one or more of a film, a laminate, a foam, an injection molded thermoplastic, a vacuum thermoformed material, a fibrous structure, and hybrids thereof. The adjunct can also include one or more biologically-derived materials, and/or synthetic materials, and/or one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Gelatin can also be used and processed into a foam. Examples of various foam adjuncts are further described in previously mentioned U.S. Pat. No. 8,393,514 entitled "Selectively Orientable Implantable Fastener Cartridge" and filed Sep. 30, 2010.

An adjunct can also be formed from a film formed from any suitable material or combination thereof discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways. For example, it can be an extruded or a compression molded film. The medicants can also be adsorbed onto the film via non-covalent interactions such as hydrogen bonding.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct. The adjunct can be formed from woven, knitted, or otherwise interconnected fibers, which allows the adjunct to be stretched. For example, the adjunct can be configured to stretch in a direction along its longitudinal axis and/or in a lateral direction that is perpendicular to the longitudinal axis. While being stretchable in at least two dimensions (e.g., X and Y directions), the adjunct can provide reinforcement along its thickness (e.g., a Z direction) such that it stretches but resists tearing and pull-through by the staples. Non-limiting examples of adjuncts that are configured to be implanted such that they can stretch with the tissue are described in the above-mentioned U.S. Pat. Pub. No. 2016/0089142 entitled "Method for Creating a Flexible Staple Line," filed on Sep. 26, 2014, which is hereby incorporated by reference herein in its entirety.

The adjunct can also be a hybrid construct, such as a laminate composite or melt-locked interconnected fiber. Examples of various hybrid construct adjuncts are further described in U.S. Pat. No. 9,282,962 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

The adjuncts in accordance with the described techniques can be formed from various materials. The materials can be used in various embodiments for different purposes. The materials can be selected in accordance with a desired therapy to be delivered to tissue so as to facilitate tissue in-growth. The materials can include bioabsorbable and biocompatible polymers, including homopolymers and copolymers. Bioabsorbable polymers can be absorbable, resorbable, bioresorbable, or biodegradable polymers. An adjunct can also include active agents, such as active cell culture (e.g., diced autologous tissue, agents used for stem cell therapy (e.g., Biosutures and Cellerix S.L.)), hemostatic agents, and tissue healing agents.

The adjuncts can releasably retain therein at least one medicant that can be selected from a large number of different medicants. Medicants include, but are not limited to, drugs or other agents included within, or associated with, the adjunct that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response. The adjuncts can also be made from or include agents that enhance visibility during imaging, such as, for example, echogenic materials or radio-opaque materials.

Examples of various adjuncts and various techniques for releasing medicants from adjuncts are further described in U.S. patent application Ser. No. 14/840,613 entitled "Medicant Eluting Adjuncts and Methods of Using Medicant Eluting Adjuncts" and filed Aug. 31, 2015, which is hereby incorporated by reference in its entirety.

While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct(s) can be configured to wick or absorb beneficial fluids, e.g., sealants, blood, glues, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts. The adjunct(s) may also affect tissue growth through the spacing, positioning and/or orientation of any fibers or strands associated with the adjunct(s).

Adjunct Attachment

In general, when using an adjunct in conjunction with a surgical stapler, the adjunct can be removably attached to the end effector. The adjunct will preferably remain secured to the end effector while the end effector is positioned at a treatment site, and is removed from the end effector when staples are deployed at the treatment site to provide the benefits discussed above. However, it has been observed that adjuncts can prematurely detach from the end effector prior to staple deployment. Detachment of the adjunct from the end effector can occur in various forms, depending on the manner in which the end effector is used. For example, detachment can include vertical lift off of the adjunct from the end effector, lateral sliding of the adjunct with respect to the end effector, and/or curling of the edges of the adjunct from the surface of the end effector. The adjunct can also slide sideways when an end effector is used to clamp and twist tissue.

FIGS. 5-9 illustrate various exemplary devices and methods for attaching an adjunct to a surgical instrument. In general, an adjunct can include a plurality of suction members configured to attach the adjunct to an end effector jaw of surgical instrument by a suction force/partial vacuum, which in certain aspects can be generated when the adjunct is compressed against the end effector jaw. The suction members can be further configured to release the suction/partial vacuum, decoupling the adjunct from the end effector jaw at a treatment site. Embodiments of the adjuncts are discussed below in conjunction with the stapler 10, where the suction members couple the adjunct to a tissue contacting surface 33 of the upper jaw 34 of an end effector 30. However, a person skilled in the art will appreciate that embodiments of the suction members can be employed with any surgical instrument without limit. Furthermore, embodiments of the suction members can be employed to couple adjuncts with the tissue contacting surface 33 of the upper jaw 34, a tissue contacting surface of the lower jaw 32, and combinations thereof.

Figure 5:
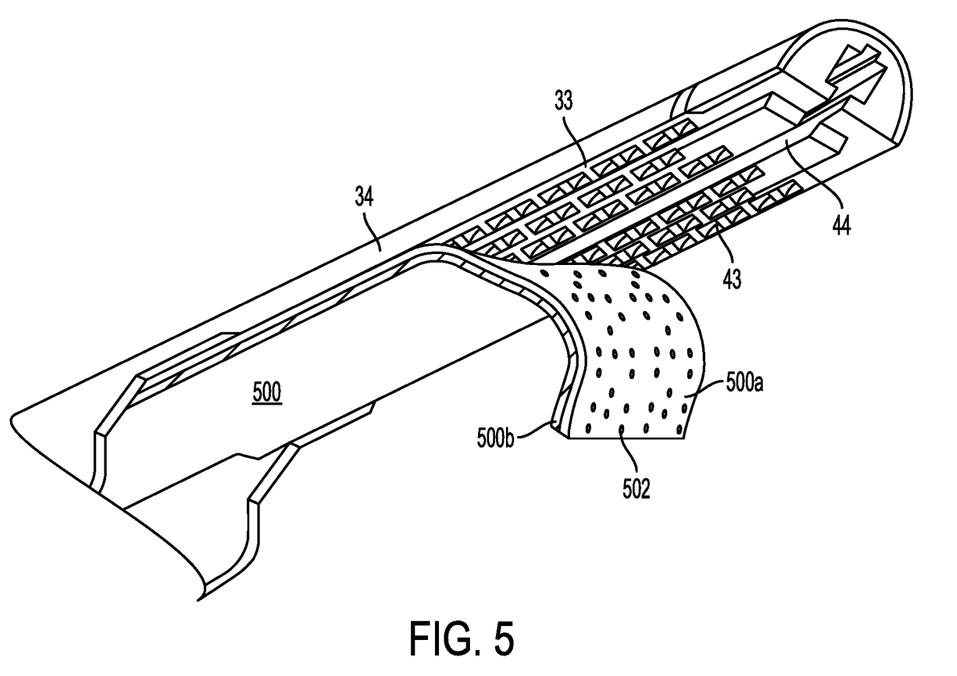
FIG. 5 is a perspective view of one embodiment of an adjunct coupled to an end effector jaw by suction.
Figure 6A:
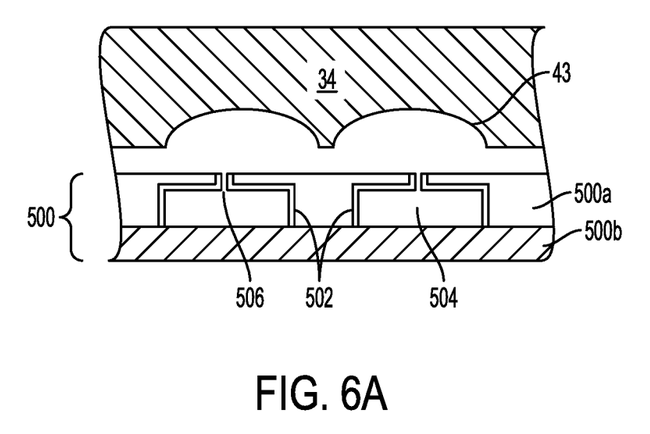
FIG. 6A is a cross-sectional view of the end effector jaw and adjunct of FIG. 5 showing the adjunct prior to contact with a tissue contacting surface of the jaw.
Figure 6B:
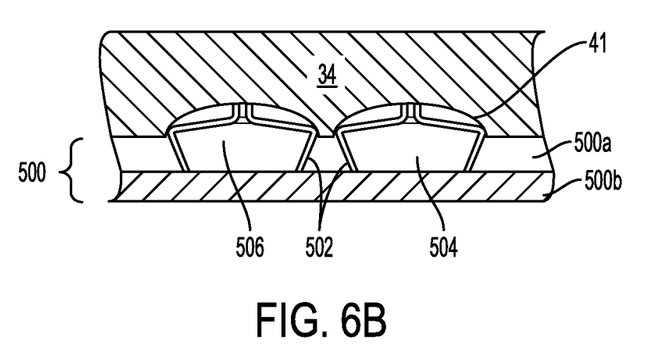
FIG. 6B is a cross-sectional view of the end effector jaw and adjunct of FIG. 6A showing the adjunct attached to the tissue contacting surface of the jaw by suction.
Figure 6C:
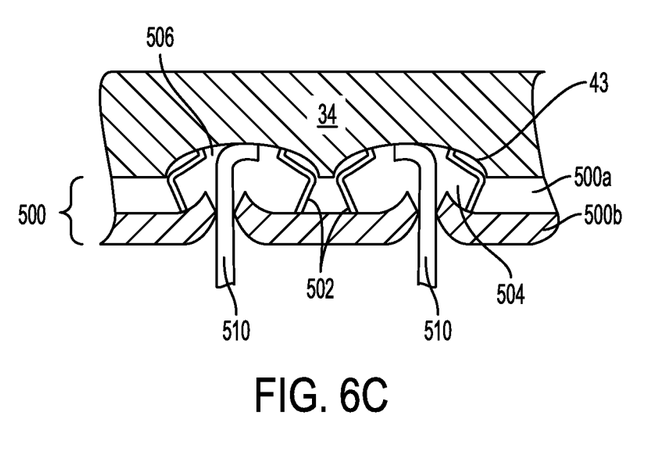
FIG. 6C is a cross-sectional view of the end effector jaw and adjunct of FIG. 6A showing the adjunct punctured by staples.

FIGS. 5-6C illustrate an embodiment of an adjunct 500 that includes a plurality of suction members 502 disposed upon the tissue contacting surface 33 (e.g., an anvil surface) of the upper jaw 34 of stapling device 10. As described in detail below, each of the suction members 502 can be formed within the adjunct 500 and can be configured to couple the adjunct 500 to the upper jaw 34. For example, the suction members 502 can provide a suction force/partial vacuum between the adjunct 500 and the tissue contacting surface 33 that is sufficient to inhibit lateral sliding and vertical removal of the adjunct 500 with respect to the tissue contacting surface 33 prior to placement at a treatment site.

In the embodiment shown in FIGS. 5-6C, the adjunct 500 can be formed as a flexible laminate, including a first adjunct layer 500a and a second adjunct layer 500b. The first and second adjunct layers 500a, 500b can be coupled together along a common interface. In an exemplary embodiment, the first adjunct layer 500a includes the plurality of suction members 502 and the second adjunct layer 500b is substantially solid, non-permeable, and void-free. The plurality of suction members 502 include a plurality of air pockets or voids 504 formed beneath the surface of the first adjunct layer 500a and respective openings 506 formed in an outer surface of the first adjunct layer 500a. While the first and second adjunct layers 500a, 500b are illustrated as single layers, a person skilled in the art will appreciate that either or both of the first and second adjunct layers can be formed from two or more discrete layers fused together.

The plurality of suction members 502 can be formed in a variety of ways. In one embodiment, the voids 504 can be formed by cutting pockets having a selected shape through an inner surface and into a bulk of the first adjunct layer 500a, separated from the outer surface by a selected distance. In another embodiment, the first adjunct layer can be cast from a melt using a mold that defines the pockets and, optionally, the openings 506 therein. In either scenario, respective openings 506 can be further formed through each of the pockets to the outer surface of the first adjunct 500a. A diameter of each opening 506 can be less than its corresponding pocket. Once the pockets and openings 506 are formed, the first adjunct layer 500a can be placed on the second adjunct layer 500b and coupled thereto to close the pockets on all sides except for the openings 506, forming the voids 504. For example, the first and second adjunct layers 500a, 500b can be fused together along a common interface including the inner surface of the first adjunct layer 500a by one or more of application of heat, adhesives, activation of the first and/or second adjunct layers 500a, 500b by a solvent, and any other mechanism for lamination of the first and second adjunct layers 500a, 500b. A person skilled in the art will appreciate that, while FIGS. 5 and 6A-6C illustrate the plurality of voids 504 as having rectilinear shapes, they can adopt any desired shape.

A suction force/partial vacuum can be generated between the suction members 502 and the tissue contacting surface 33 as follows. As illustrated in FIG. 6A, the adjunct 500 can be oriented with the outer surface of the first adjunct layer 500a opposite the tissue contacting surface 33 of the upper jaw 34. Subsequently, the adjunct 500 can be positioned on the upper jaw 34, with the first adjunct layer 500a contacting the tissue contacting surface 33, and the second adjunct layer 500b can be compressed against the tissue contacting surface 33, as illustrated in FIG. 6B. This compression can establish a partial vacuum within the plurality of voids 504 by elastically deforming the plurality of voids 504 and expelling air from the plurality of voids 504 to the environment via the plurality of openings 506. Since the pressure of the surrounding atmosphere is greater than the pressure within the plurality of voids 504, the atmosphere presses the plurality of voids 504 against the tissue contacting surface 33, establishing the suction force/partial vacuum that secures the adjunct 500 to the upper jaw 34. A person skilled in the art will appreciate that, while the adjunct 500 is illustrated as a laminate in FIGS. 5-6C, alternative embodiments of the adjunct can be formed as a single layer that includes the plurality of suction members 502.

The adjunct 500 can be formed from one or more materials configured to allow flexure of the adjunct 500 and deformation (e.g., elastic deformation) of the adjunct 500 under compression. For example, the first and second adjunct layers 500a, 500b can each be independently selected from materials possessing a stiffness that provides a desired degree of elastic deformation under flexure and/or compression. Examples of suitable materials can include, but are not limited to, synthetic materials and biologic materials. Synthetic materials can include biodegradable polymers such as polydioxanone (PDS), Monocryl® (poliglecaprone 25, a copolymer of glycolide and ε-caprolactone; Ethicon, Inc.), polyhydroxy acids (e.g., polylactides, polyglycolides, polyhydroxybutyrates, polyhydroxy-valeriates), copolymers of lactide and trimethylene carbonate, copolymers of glycolide, lactide and trimethylene carbonate, polycaprolactones, polydioxanones, synthetic or natural oligo- and polyamino acids, polyphosphazenes, polyanhydrides, polyorthoesters, polyphosphates, polyphosphonates, polyalcohols, polysaccharides, and polyethers. Biologic materials can include, but are not limited to, naturally-occurring materials (e.g., collagens, gelatin), naturally-derived materials (e.g., bioabsorbable gel films cross-linked with omega-3 fatty acids), and oxygenized regenerated cellulose (ORC). In certain embodiments, a thickness of each of the first and second adjunct layers 500a, 500b can be independently selected from the range of about 8 μm to about 25 μm. The arrangement of the suction members 502 within the adjunct 500 can be configured to facilitate deformation of the adjunct 500 under compression. For example, as further illustrated in FIG. 6B, at least a portion of the suction members 502 can be formed in a pattern that substantially matches a pattern of staple-receiving cavities 43 formed in the tissue contacting surface and aligned with the staple-receiving cavities 43 when positioned on the upper jaw 34. The suction members 502 aligned in this manner can be more easily compressed against the upper jaw 34, as compared to suction members 502 that are not aligned because they are not supported by the upper jaw 34 (e.g., the tissue contacting surface 33 is recessed from the first adjunct layer 500a by the staple-receiving cavities 43). One skilled in the art will appreciate alternative embodiments of the suction members 502 can alternatively or additionally be patterned for alignment with the pockets 41 of the tissue contacting surface of the lower jaw 32.

The adjunct 500 can also be applied to the tissue contacting surface 33 using an applicator (not shown) that facilitates compression of the adjunct 500. The applicator can include raised areas having a similar shape and/or distribution pattern as the staple-receiving cavities 43. When a raised area of the applicator is aligned with a given suction member 502 and staple-receiving cavity 43, the raised area can extend within the staple-receiving cavity 43 and compress the suction member 502 by a greater degree than a planar applicator. One skilled in the art will appreciate alternative embodiments of the applicator can be patterned for alignment with the pockets 41 of the tissue contacting surface of the lower jaw 32.

The suction members 502 can also be configured in a variety of ways to adjust the suction force/partial vacuum. In one example, the suction force/partial vacuum of a given suction member 502 can be raised or lowered by increasing or decreasing the volume of the plurality of voids 504, assuming a constant pressure difference between the atmosphere and the plurality of voids 504. In another example, the total suction force exerted on the adjunct 500 by the plurality of suction members 502 can be raised or lowered by increasing or decreasing the number of suction members 502 within the adjunct 500, assuming each suction member 502 is the same volume. Furthermore, by varying the location of suction members 502 within the adjunct 500, the suction force/partial vacuum can be locally increased or decreased at selected areas of the adjunct 500.

The suction members 502 can be further configured to release the adjunct 500 from the tissue contacting surface 33 after penetration of staples through the adjunct 500, allowing the adjunct 500 to be retained at a tissue treatment site when the end effector 30 is retracted from the tissue. In one embodiment, the suction force/partial vacuum exerted by the plurality of suction members 502 can be tailored, as discussed above, so that the force with which the adjunct 500 is attached to the tissue by the staples is greater than the suction force. Thus, after the staples are deployed through the adjunct 500 and the tissue, the adjunct 500 can be released from the tissue contacting surface 33. In another embodiment, illustrated in FIGS. 6B-6C, at least a portion of the suction members 502 can be aligned with respective staple-receiving cavities 43. In an exemplary embodiment (FIG. 6C), staples 510 fired through the adjunct 500 and into the staple-receiving cavities 43 can pierce the plurality of voids 504 to break the suction/partial vacuum.

Embodiments of the adjunct 500 can optionally include one or more features configured to work in combination with suction members 502 to inhibit sliding of the adjunct 500 when positioned on the tissue contacting surface 33. For example, the adjunct 500 can include one or more protruding features (not shown) that extend outward from the surface of the first adjunct layer 500a. These features can be dimensioned for receipt within one or more recessed areas formed within the tissue contacting surface 33. As shown in FIG. 5, one embodiment of the recessed areas can include a slot 44 formed in the upper jaw 34 that is configured to receive the knife blade 36 or other cutting element during advancement between the jaws 32, 34. When the adjunct 500 is positioned on the tissue contacting surface 33 one or more protruding features can extend within the slot 44 and maintain the lateral position of the adjunct 500 when experiencing shear stresses. The suction members 502 can be distanced from the location of the protruding features to avoid interference with compression of the suction members 502.

Figure 7A:
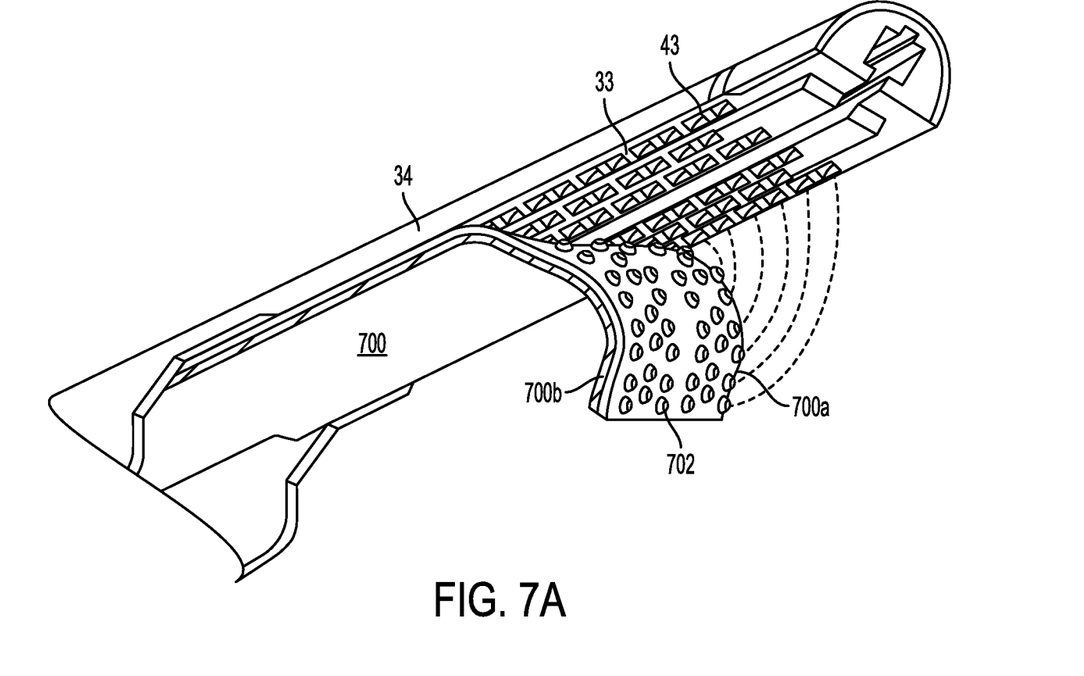
FIG. 7A is a perspective view of another embodiment of an adjunct coupled to an end effector jaw by suction.

Another embodiment of an adjunct 700 is illustrated in FIGS. 7A-8C. The adjunct can generally be configured and used similar to the adjunct 500, attaching to the tissue contacting surface 33 via suction force/partial vacuum and releasing from the tissue contacting surface 33 when staples are deployed. As shown in FIGS. 7A-7B, the adjunct 700 includes coupled first and second adjunct layers 700a, 700b and a plurality of suction members 702. In this implementation, the suction members 702 can be formed as hollow protrusions extending outward from a surface of the first adjunct layer 700a, opposite the second adjunct layer 700b. The protrusions can define a plurality of air pockets 704 in fluid communication with respective openings 706 extending through each protrusion. While the first and second adjunct layers 700a, 700b are illustrated as single layers, a person skilled in the art will appreciate that either or both of the first and second adjunct layers can be formed from two or more discrete layers fused together.

Figure 8A:
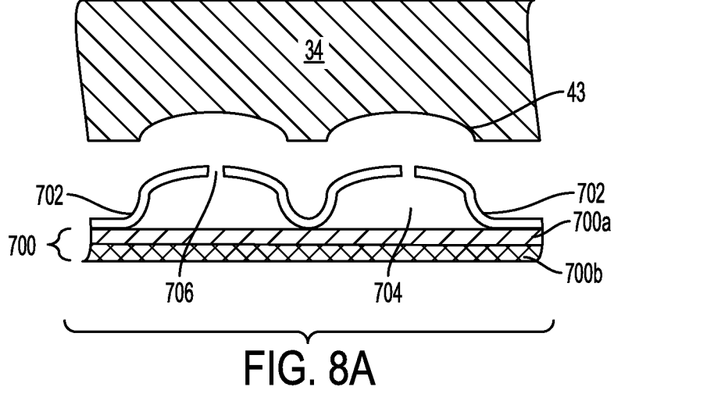
FIG. 8A is a cross-sectional view of the end effector jaw of FIG. 7A showing the adjunct prior to contact with a tissue contacting surface of the jaw.
Figure 8B:
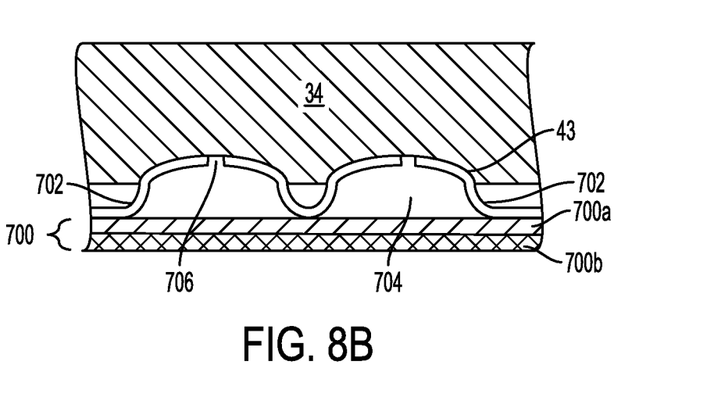
FIG. 8B is a cross-sectional view of the end effector jaw and adjunct of FIG. 8A showing the adjunct attached to the tissue contacting surface of the jaw by suction.
Figure 8C:
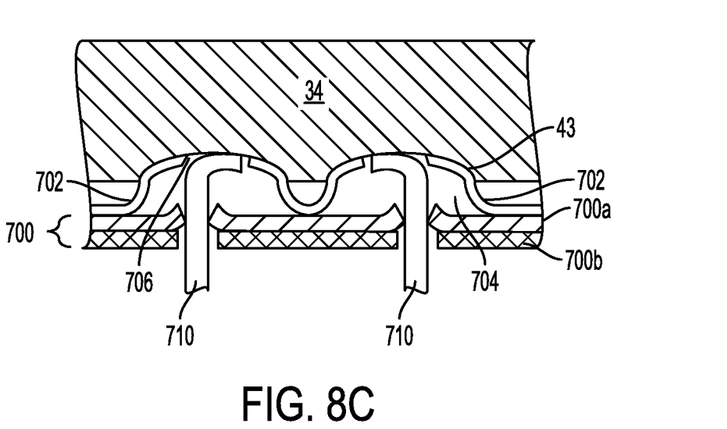
FIG. 8C is a cross-sectional view of the end effector jaw and adjunct of FIG. 8A showing the adjunct punctured by staples.
Figure 9:
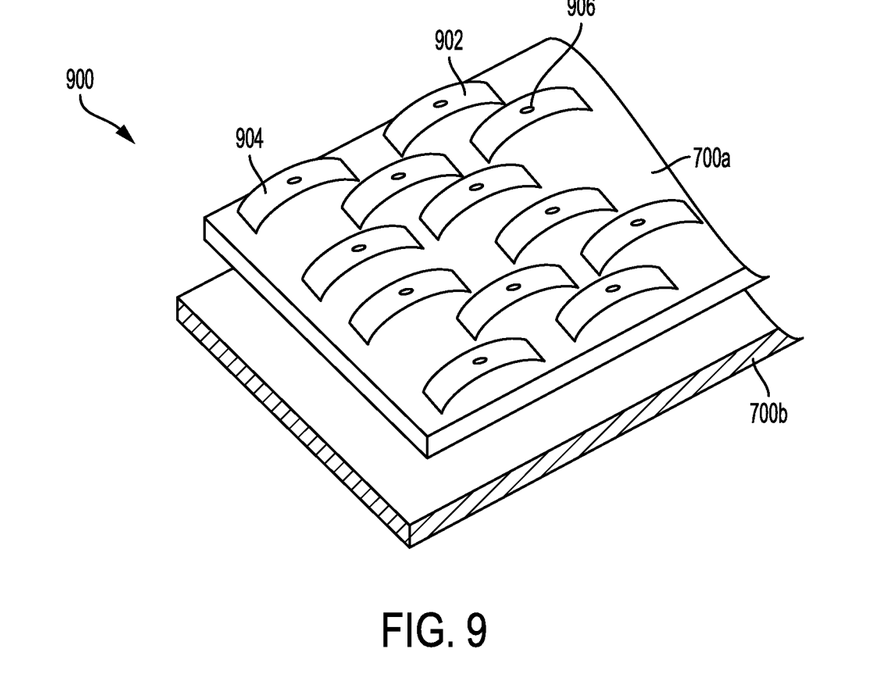
FIG. 9 is a perspective disassembled view of a portion of an adjunct according to another embodiment.

As shown in FIGS. 8A-8C, the adjunct 700 can be positioned on the tissue contacting surface (FIG. 8A) and suction members 702 can be compressed to expel air from the air pockets 704 to the environment via the openings 706, forming a suction force/partial vacuum therein (FIG. 8B). The air pockets 704 can further release the suction resulting from the partial vacuum when the staples are fired through the adjunct 700. In an exemplary embodiment, the suction force/partial vacuum can be released by piercing the air pockets 704 with staples 710, as shown in FIG. 8C. Alternatively or additionally, the force of the suction/partial vacuum provided by the plurality of suction members 702 can be overcome by the strength of attachment of the staples 710 to tissue (not shown) when the end effector 30 is removed from the tissue. A person skilled in the art will appreciate that, while FIGS. 7A-8C illustrate the plurality of suction members 702 as having generally circular shapes, the suction members 702 can adopt any desired shape. For example, FIG. 9 illustrates an embodiment of an adjunct 900 that includes a plurality of suction members 902 with air pockets 904 formed therein and having openings 906. As shown, the suction members 902 have a shape that conforms to the shape of the staple-receiving cavities 43.

Figure 7B:
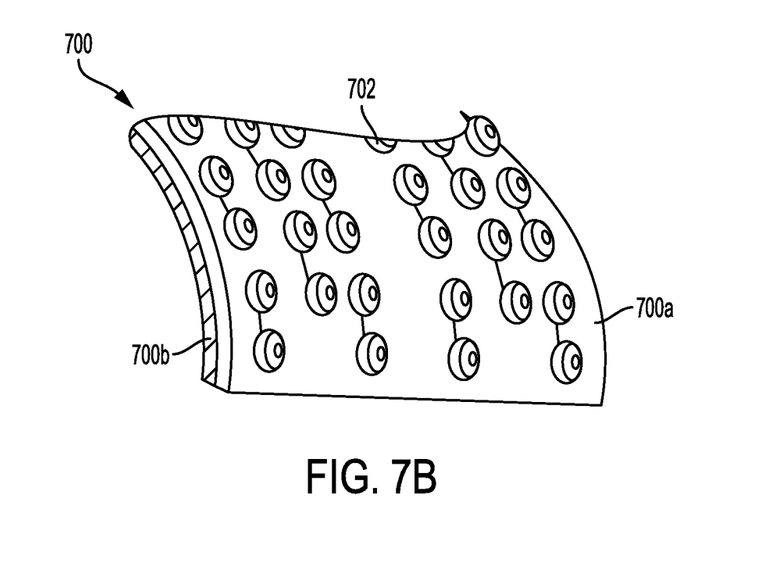
FIG. 7B is a perspective disassembled view of a portion of the adjunct of FIG. 7A.

The plurality of suction members 702, 902 can be formed in a variety of ways. In one embodiment, protrusions can be formed by casting the first adjunct layer 700a from a melt using a mold that defines voids having a selected shape therein. Subsequently, respective openings 706, 906 can be formed through each of the voids to the outer surface of the first adjunct 700a. A diameter of each opening 706, 906 can be less than a width of its corresponding void. After the voids and openings 706, 906 are formed, the first adjunct layer 700a can be placed on the second adjunct layer 700b and coupled thereto to close the voids on all sides except for the openings 706, 906, forming the air pockets 704, 904. For example, the first and second adjunct layers 700a, 700b can be fused together along a common interface including the inner surface of the first adjunct layer 700a by one or more of application of heat, adhesives, activation of the first and/or second adjunct layers 500a, 500b by a solvent, and any other mechanism for lamination of the first and second adjunct layers 700a, 700b.

The plurality of suction members 702, 902 can also be configured to inhibit lateral sliding of the adjuncts 700, 900 when positioned on the upper jaw 34. In one embodiment, at least a portion of the suction members 702, 902 can possess a shape dimensioned for receipt within the plurality of staple-receiving cavities 43. For example, the shape of the suction members 902 can be configured to mate with the plurality of staple-receiving cavities 43. In these implementations, when the suction members 702, 902 are received within the staple-receiving cavities 43 and the adjunct 700 is subjected to in-plane forces (e.g., shear forces), the lateral sides of the staple-receiving cavities 43 can constrain the lateral motion of the suction members 702, 902, thereby inhibiting lateral motion of the adjuncts 700, 900.

In an embodiment, any of the adjuncts 500, 700, 900 can also be configured to perform a healing function when positioned on tissue. Such healing functions can include, but are not limited to, delivering a medicant, reinforcing tissue, promoting tissue ingrowth or adhesions, deter adhesions, and the like.

Terminology

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

A person skilled in the art will appreciate that the present invention has application in conventional minimally-invasive and open surgical instrumentation as well application in robotic-assisted surgery. In some embodiments, the devices and methods described herein are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

Re-Use

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed:

1. A surgical stapling device, comprising:
   an elongate shaft having an end effector with first and second jaws configured to grasp tissue therebetween, the first jaw having an anvil with a plurality of staple-receiving cavities formed therein; and an adjunct positioned on the first jaw and having a plurality of voids configured to engage the anvil of the first jaw by a suction force, each of the plurality of voids being formed in a hollow protrusion extending outward from a surface of the adjunct;

wherein the plurality of voids are aligned with the plurality of staple-receiving cavities such that each void is configured to be received in and compressed against a staple-receiving cavity to generate the suction force that causes the adjunct to engage the anvil of the first jaw.

2. The device of claim 1, wherein the end effector is configured to fire a plurality of staples through the adjunct to release the suction force and thereby cause the adjunct to be released from the end effector.

3. The device of claim 1, wherein the adjunct includes first and second layers laminated together, the plurality of voids being formed in the first layer and the first layer being positioned in contact with a surface of the first jaw.

4. The device of claim 1, wherein the end effector is configured to fire a plurality of staples through the adjunct such that the plurality of staples penetrate the plurality of voids to break the suction force and release the adjunct from the end effector.

5. The device of claim 4, wherein each of the plurality of voids is aligned with a corresponding leg of one of the plurality of staples such that each leg of each staple of the plurality of staples breaks the suction force of one corresponding void of the plurality of voids.

6. The device of claim 1, wherein the first jaw includes a plurality of alignment features configured to align the plurality of protrusions with the plurality of staple-receiving cavities.

7. The device of claim 1, wherein each hollow protrusion has a semi-spherical shape.

8. The device of claim 1, wherein each hollow protrusion has an opening formed therethrough connecting the corresponding void with an external environment surrounding the surgical stapling device, and each opening has a smaller perimeter than a perimeter of each void.

9. A surgical stapling device, comprising:

an elongate shaft having an end effector with first and second jaws configured to grasp tissue therebetween, the first jaw having an anvil with a plurality of staple-receiving cavities formed therein; and a flexible laminated adjunct formed from at least a first layer coupled to a second layer, the first layer having an outermost surface and a plurality of suction members protruding therefrom, each suction member having an air pocket formed therein and having an opening formed between the corresponding air pocket and an external environment surrounding the surgical stapling device, each opening having a smaller perimeter than a perimeter of each air pocket;

wherein the plurality of suction members is configured to be received within the plurality of staple-receiving cavities on the anvil to generate a partial vacuum within each air pocket.

10. The device of claim 9, wherein each of the plurality of suction members is configured to be received in and compressed against a corresponding cavity of the plurality of staple-receiving cavities on the anvil to generate the partial vacuum within each air pocket.

11. The device of claim 9, wherein the end effector is configured to fire a plurality of staples through the adjunct to release the partial vacuum within each air pocket and thereby cause the adjunct to be released from the end effector.

12. The device of claim 9, wherein the first layer is elastically deformable.

13. The device of claim 9, wherein compressing the adjunct is configured to cause air in the plurality of air pockets to flow out of the plurality of openings to generate the partial vacuum.

14. The device of claim 9, wherein the second adjunct layer comprises a solid, non-permeable, void-free layer.

15. The device of claim 9, wherein each suction member has a dome shape, and each opening is formed at a top of each corresponding dome.

* * * * *